US008599025B2

(12) United States Patent
Cipriano

(10) Patent No.: US 8,599,025 B2
(45) Date of Patent: Dec. 3, 2013

(54) SYSTEM AND METHOD TO DETERMINE AN INFANT WEIGHT WHILE MINIMIZING DISTURBANCE TO THE INFANT

(75) Inventor: James P. Cipriano, Laurel, MD (US)

(73) Assignee: General Electric Company, Schenectady, NY (US)

( * ) Notice: Subject to any disclaimer, the term of this patent is extended or adjusted under 35 U.S.C. 154(b) by 504 days.

(21) Appl. No.: 12/984,005

(22) Filed: Jan. 4, 2011

(65) Prior Publication Data
US 2012/0169501 A1 Jul. 5, 2012

(51) Int. Cl.
G08B 23/00 (2006.01)

(52) U.S. Cl.
USPC .............. 340/573.1; 177/25.19; 702/173

(58) Field of Classification Search
USPC ............ 340/573.1, 539.12, 613, 666, 286.07; 73/290; 702/173; 705/2, 3; 177/28.16
See application file for complete search history.

(56) References Cited

U.S. PATENT DOCUMENTS

| 4,038,973 | A | * | 8/1977 | Moore | 600/22 |
| 4,347,903 | A | * | 9/1982 | Yano et al. | 177/25.13 |
| 4,366,873 | A | * | 1/1983 | Levy et al. | 177/25.19 |
| 4,412,298 | A | * | 10/1983 | Feinland et al. | 702/102 |
| 5,376,761 | A | | 12/1994 | Koch et al. | |
| 5,673,691 | A | * | 10/1997 | Abrams et al. | 600/300 |
| 6,215,078 | B1 | * | 4/2001 | Torres et al. | 177/25.15 |
| 6,538,215 | B2 | * | 3/2003 | Montagnino et al. | 177/25.15 |
| 6,956,175 | B1 | * | 10/2005 | Daly et al. | 177/1 |
| 7,194,301 | B2 | * | 3/2007 | Jenkins et al. | 607/2 |
| 7,253,366 | B2 | * | 8/2007 | Bhai | 177/45 |
| 7,357,811 | B2 | | 4/2008 | Dykes et al. | |
| 7,364,539 | B2 | * | 4/2008 | Mackin et al. | 600/22 |
| 7,395,183 | B2 | * | 7/2008 | Hamamoto | 702/173 |
| 7,442,163 | B2 | | 10/2008 | Ten Eyck et al. | |
| 7,533,799 | B2 | * | 5/2009 | Edwards | 235/375 |
| 8,280,719 | B2 | * | 10/2012 | Miller | 704/9 |
| 2002/0134589 | A1 | * | 9/2002 | Montagnino et al. | 177/25.16 |
| 2006/0015016 | A1 | * | 1/2006 | Thornton | 600/300 |

FOREIGN PATENT DOCUMENTS

| DE | 3534559 | A1 | 4/1987 |
| EP | 0628795 | A1 | 12/1994 |
| EP | 1795121 | A2 | 6/2007 |

OTHER PUBLICATIONS

Search Report from corresponding GB Application No. 1122182.7, dated Jun. 14, 2012.

* cited by examiner

Primary Examiner — Jennifer Mehmood
Assistant Examiner — Rufus Point
(74) Attorney, Agent, or Firm — Andrus, Sceales, Starke & Sawall, LLP

(57) ABSTRACT

A method and system for determining the weight of an infant when the infant is either placed upon a support platform or removed from the support platform, where the support platform may be configured as a bed. A sensor is positioned beneath the support platform that provides a weight measurement to a control unit. The control unit determines a baseline weight for the bed and any object placed on the bed. The control unit calculate a recent weight estimate and determines whether the recent weight estimate is different from the baseline weight by more than a weight threshold. If the difference is greater than the weight threshold, the system generates a weight estimate to a user. Once the weight estimate has been generated, the system adjusts the weight threshold such that the adjusted weight threshold is used in additional processing and calculations of the infant weight.

19 Claims, 7 Drawing Sheets

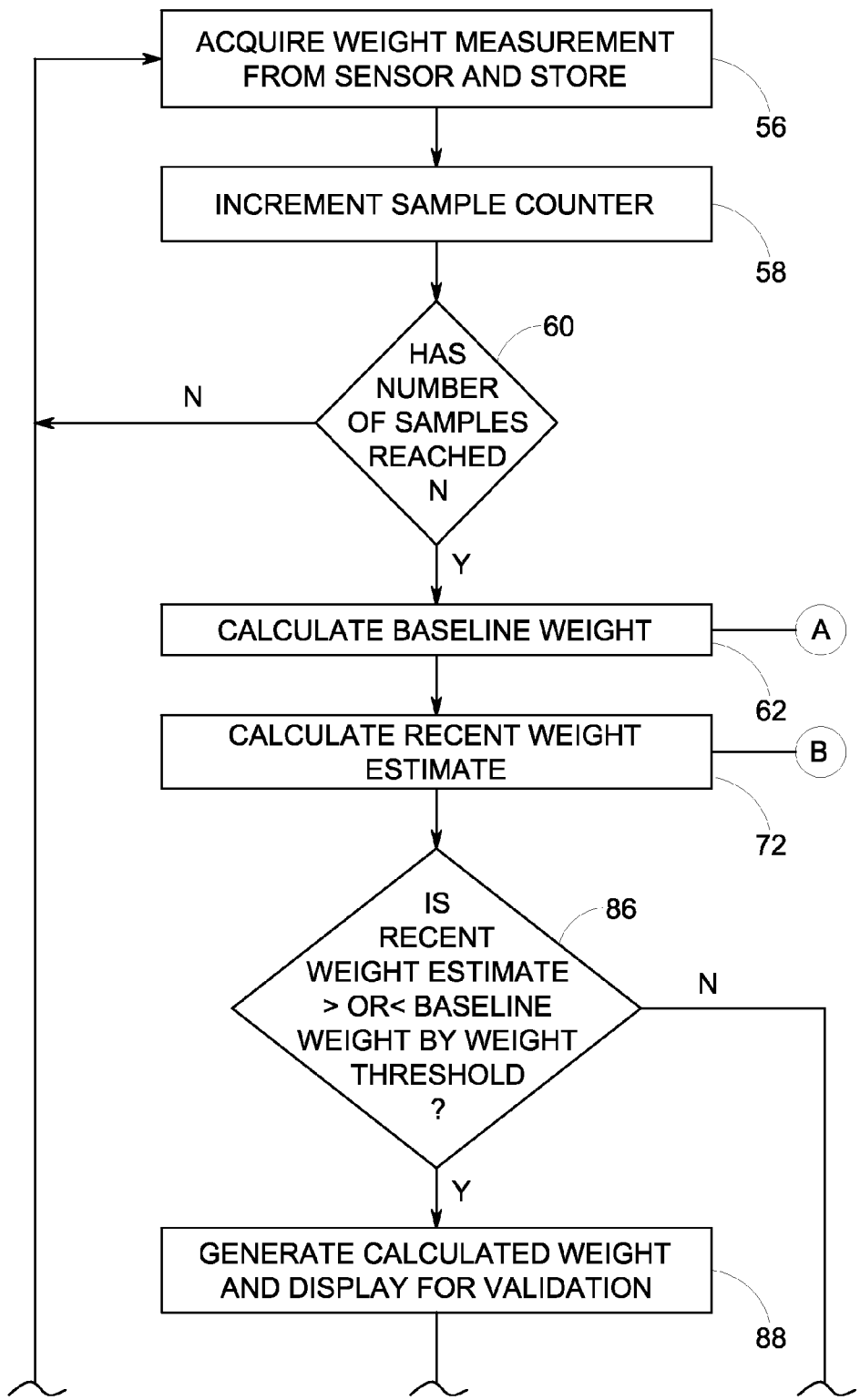
FIG. 4 (Continued on next page)

SYSTEM AND METHOD TO DETERMINE AN INFANT WEIGHT WHILE MINIMIZING DISTURBANCE TO THE INFANT

BACKGROUND OF THE INVENTION

The present disclosure generally relates to a method and apparatus for accurately weighing a patient, such as an infant. More specifically, the present disclosure relates to a method and apparatus that accurately determines the weight of an infant whenever the infant is placed on a bed or an incubator or removed from the bed or incubator.

Premature infants are often placed within an incubator so that they may have a controlled and monitored environment to aid in their survival and growth. Premature infants are fragile and, as such, highly susceptible to stress placed upon them every time they are disturbed by physical contact such as is required for lifting, moving or performing tests. This stress can contribute to a higher incidence of complications and possibly extend the hospital stay. Studies have shown that neonates, on average, get less than 30 minutes per day of quality rest. Infants that receive more rest are shown to recover faster Nevertheless, it is often necessary to physically contact the infant. For example, infants, irrespective of their degree of prematurity, are often briefly placed in warmers. This is done so that while care is given, the infant is warmed by overhead heaters, and may also receive phototherapy, for example to treat jaundice. It is also often necessary to monitor the infant's weight. For example, medical therapies, such as the proper dosing of a medication, are based upon the accurate determination of the infant's weight.

Traditionally, methods of weighing infants require removal of the infant from one environment, such as an incubator, placing the infant on a scale for weighing, and returning the infant to the prior environment. The typical sequence of events when using such scales is that the scale is first activated (usually by the pressing of a key) and scale is then calibrated to zero. Such an in-bed scale requires the infant to be lifted from the bed to initiate the weighing process. Once the patient has been lifted, the scale is calibrated to a zero reading, which takes into account all of the items currently on the bed. Once the scale has been zeroed, the patient is placed on the bed and the weight of the patient is displayed. It can be appreciated that this sequence of events requires removing the infant from the incubator, for example, and thus disturbs the infant. Another common type of available in-bed scale allows the weight of the infant to be determined when the infant is on the bed without having to disturb the patient. However, in such a system, all extraneous items, such as pacifiers, beanie infants, pillows, blankets, etc. must be removed from the bed. Further, the caregiver must try to manually negate the effect of any intravenous lines and tubing that are attached to the infant in order to provide an accurate weight.

It has been recognized that it would be desirable to have a technique for accurately weighing the infant, in both the shorter and longer term environments in which they may be placed, to assess growth and health status and without disturbing and, thus, placing unneeded stress upon the infant.

SUMMARY OF THE INVENTION

The present disclosure generally relates to a system and method for accurately weighing a patient, such as an infant. The system and method of the present disclosure calculates the weight of the infant whenever the infant is placed on a bed or removed from the bed such that the weight of the infant is determined each time the infant is moved.

The system of the present disclosure includes a support platform and sensor that support a mattress within an infant care device. The sensor generates a weight sample based upon the amount of weight on the support platform. The amount of weight on the support platform can include various different sensors and components associated with the infant when the infant is on the bed.

After a predetermined number of historic weight samples are obtained from the sensor, the control unit of the infant care device calculates a baseline weight. The calculated baseline weight includes all of the items positioned on the support platform, which may in some situations include the infant.

In addition to calculating the baseline weight, the control unit also obtains a predetermined number of current weight samples from the sensor where the current weight samples are more recent than the historic weight samples. Based upon the number of current weight samples obtained from the sensor, the control unit generates a recent weight estimate, wherein the recent weight estimate is an average of the current weight samples that are within a measurement threshold.

Once both the baseline weight and the recent weight have been calculated, the control unit determines the difference between the baseline weight and the recent weight estimate. If the infant has not recently been placed on the bed or removed from the bed, the recent weight estimate and the baseline weight estimate will be very close to each other. However, if the infant has recently been placed on the bed or removed from the bed, the recent weight estimate and the baseline weight will differ from each other. If the difference between the baseline weight and the recent weight estimate exceeds a weight threshold, the control unit will generate a calculated infant weight measurement.

Once the calculated infant weight measurement has been generated, the infant weight measurement is presented to a user for validation. The user can determine whether the weight measurement is a valid weight and confirm this determination in the control unit. When the control unit receives a validation from the user, the calculated infant weight measurement is stored in memory.

Once the calculated weight measurement is stored in memory, the control unit adjusts the weight threshold to be a preset percentage of the stored weight measurement. Thus, during future processing, the updated weight threshold will be utilized to provide a more accurate indication of whether the weight calculated is a valid weight for the infant. In this manner, the system and method of the present disclosure automatically determines the weight of an infant when the infant is either placed on the support platform or removed from the support platform. The user is presented with a calculated weight each time the infant is moved, which will reduce the number of times the infant needs to be moved to generate a weight measurement.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION OF THE INVENTION

Figure 1:
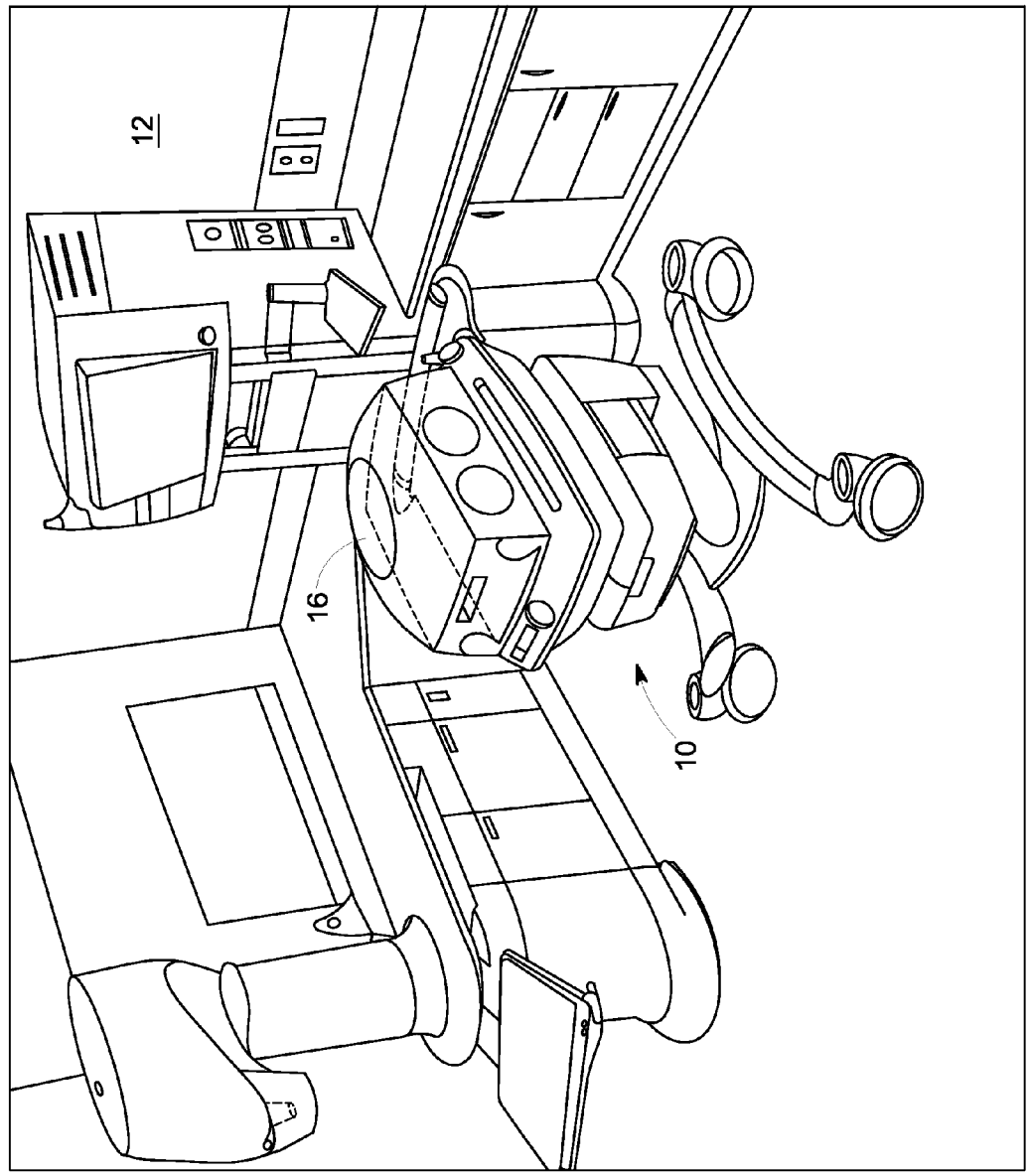
FIG. 1 is an environmental view of an infant care device.

FIG. 1 illustrates one embodiment of an infant care device 10 that incorporates the method of weighing an infant in accordance with the present disclosure. In the embodiment shown in FIG. 1, the infant care device 10 is located within a patient's room 12, which may be part of a neonatal intensive care unit (NICU). The infant care apparatus 10 shown in FIG. 1 could be many different types of devices, such as an incubator-type infant care apparatus or a patient warmer. The incubator-type device 10 shown in FIG. 1 defines a microenvironment region 16 in which the patient rests and receives therapy, including heating and possible oxygen enrichment.

Figure 2:
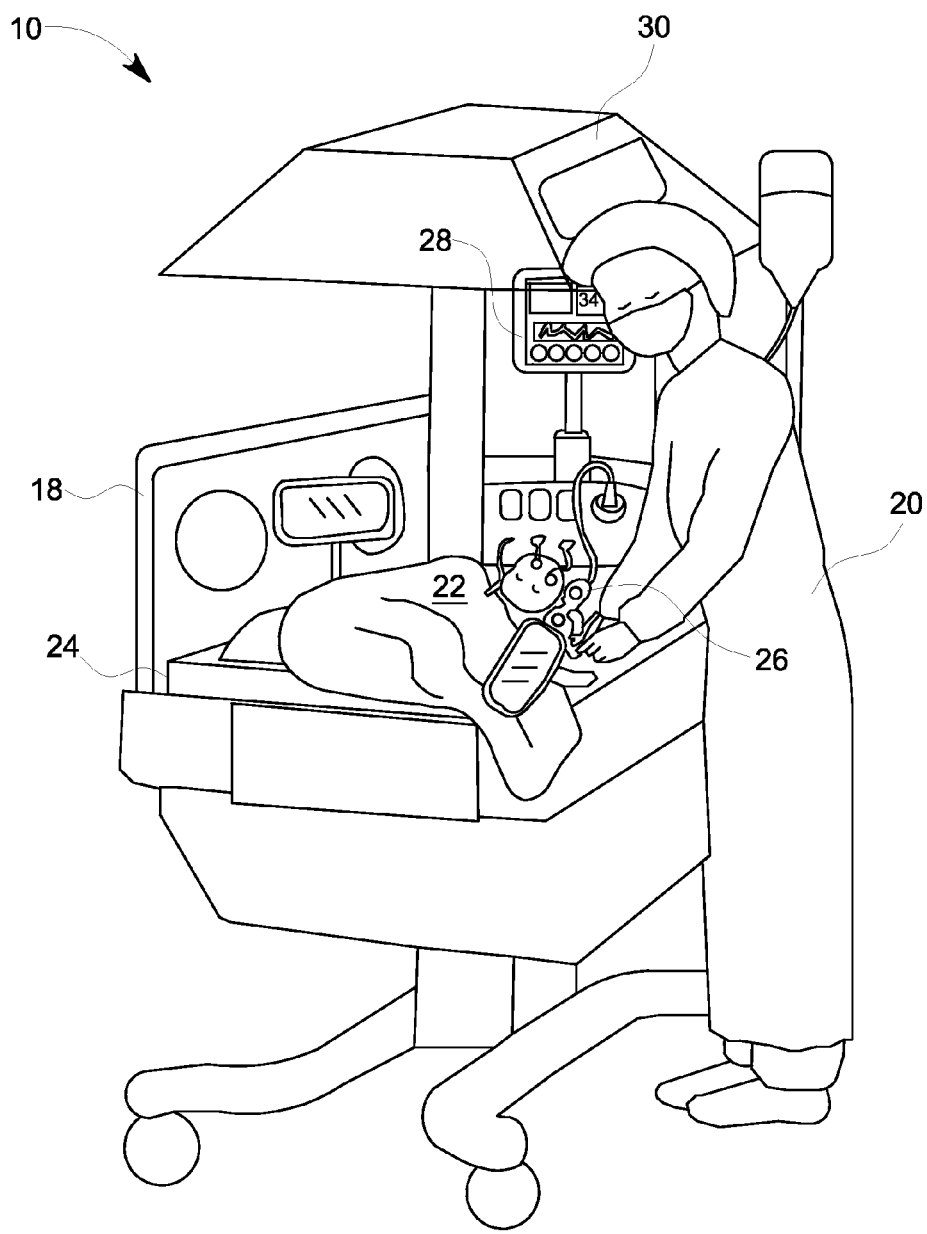
FIG. 2 is a detailed view of the infant care device including various monitoring components for an infant.

Referring now to FIG. 2, the sides 18 of the infant care device 10 can be lowered such that a caregiver 20 can have access to an infant 22 positioned on a mattress 24. Various different patient sensors 26 can be attached to the infant such that the infant care device 10 can monitor physiological parameters from the infant. The monitored physiological parameters are shown on a display 28 and can be viewed by the caregiver 20. As illustrated in FIG. 2, a relatively significant number of devices may be positioned on the mattress 24 along with the infant 22. These components can include intravenous tubes, pillows, blankets, patient sensors, and other similar components. In the embodiment shown in FIG. 2, a radiant heating hood 30 is positioned above the infant 22 and heats the infant as desired. As described previously, it is desirable that the infant 22 remain within the microenvironment created by infant care device 10 such that the patient remains warm and is disturbed as infrequently as possible.

Figure 3:
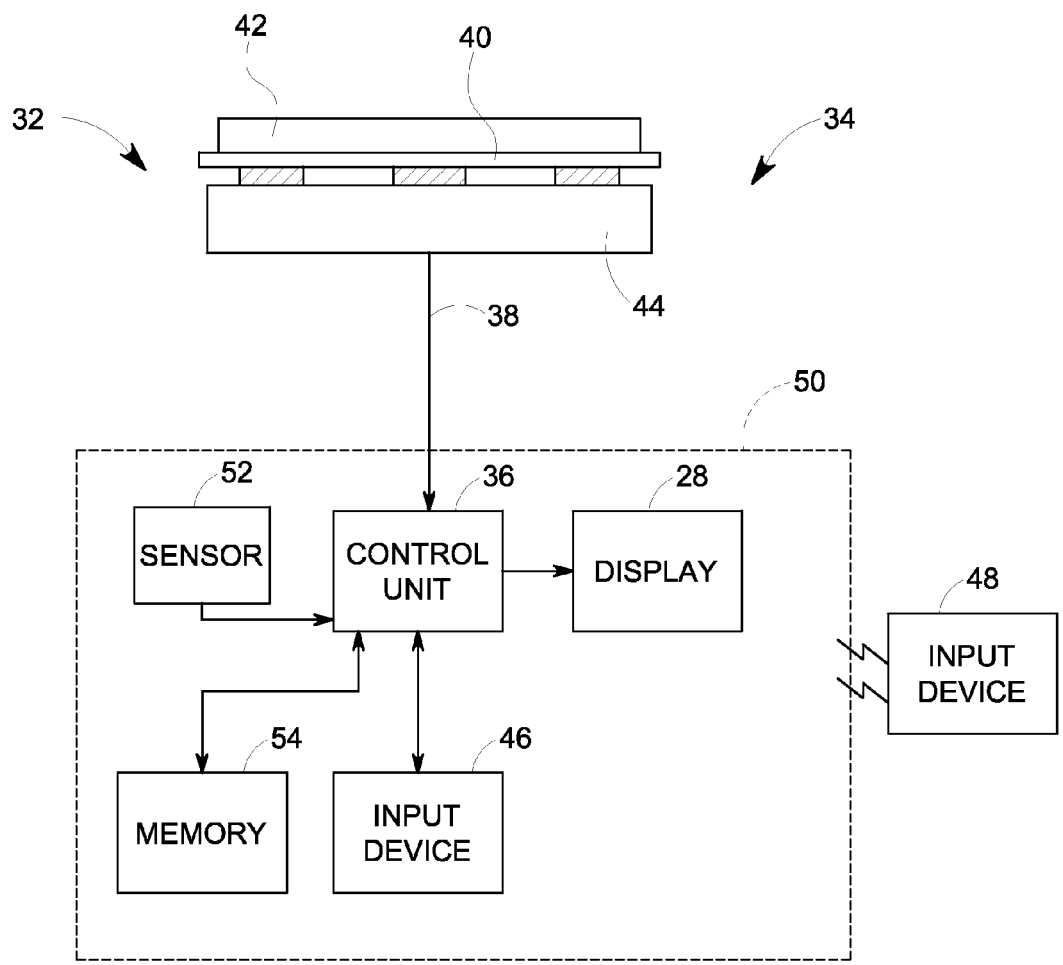
FIG. 3 is a schematic illustration of the weighing system operating in accordance with the present disclosure.

Although not shown in FIG. 2, the infant care device 10 includes a weighing system that determines the weight of the infant 22 and displays the weight on the display 28. The weighing system of the present disclosure is positioned beneath the mattress 24 and is schematically shown in FIG. 3 by reference numeral 32. The weighing system 32 includes a scale 34 and a control unit 36, which is preferably a microprocessor capable of running a processing routine. The control unit 36 could be a separate processor from the control unit of the infant care device or could be incorporated into the processor of the infant care device. The scale 34 is any conventional weighing device that is capable of outputting a signal along line 38 that is indicative of the weight of the objects placed thereon. Preferably, the scale 34 is an in-bed scale having a support platform 40 that supports the mattress 42 that is configured to fit inside the infant care device 10, either as a component of the originally manufactured equipment, as a retrofit item to an existing infant bed, or as a stand-alone unit. A sensor 44 associated with the support platform 40 outputs a signal along line 38 that is indicative of the weight supported by the platform 40, which includes the mattress, and any items positioned on the mattress, including an infant. In one embodiment of the disclosure, the sensor 44 in the scale 34 is configured as either a single or a multiple point load cell design that is accurate to within 0.01% of the load being weighed. Although the term sensor is used in the disclosure, this term should be interpreted broadly to cover any device or devices that generate a numeric representation of weight or pressure.

The weighing system 32 also includes an input device 46 that communicates with the control unit 36 for providing information to the controller, as discussed in detail below. In addition to the input device 46, a wireless input/output device 48 can be used and remotely located from the control unit 36. The wireless input/output device 48 communicates through wireless communication techniques such that the caregiver can enter information into the control unit 36 from a location remote to the housing 50 including the control unit 36 and the input device 46. As illustrated in FIG. 3, the display 28 is associated with the control unit 36 such that information from the control unit 36 can be displayed and monitored by the caregiver in the location near the infant care device. Additionally, it is contemplated that the control unit 36 could communicate with a remote location, such as a monitor at a nurses' station in the hospital or any other remote location. The data provided to the remote location from the control unit 36 can be displayed in real-time, stored in a database, processed further, or any combination thereof. In this manner, a database of weight collected for the infant associated with the infant care device 10 can be analyzed and monitored from a remote location.

The present disclosure also contemplates that the weighing system 32 could include one or more additional sensing devices 52 that allow the weighing system to come to a more accurate weight determination. As an example, the sensing device 52 could be a temperature sensor, a humidity sensor, a pressure sensor or any combination thereof to provide additional inputs to the control unit 36 such that the control unit can more accurately determine the weight of a patient. The present disclosure also contemplates that the scale includes a support platform 40 that could be tilted in either direction. In such an embodiment, the system 32 would include an inclinometer or accelerometer to measure the angle of the bed.

Figure 4:
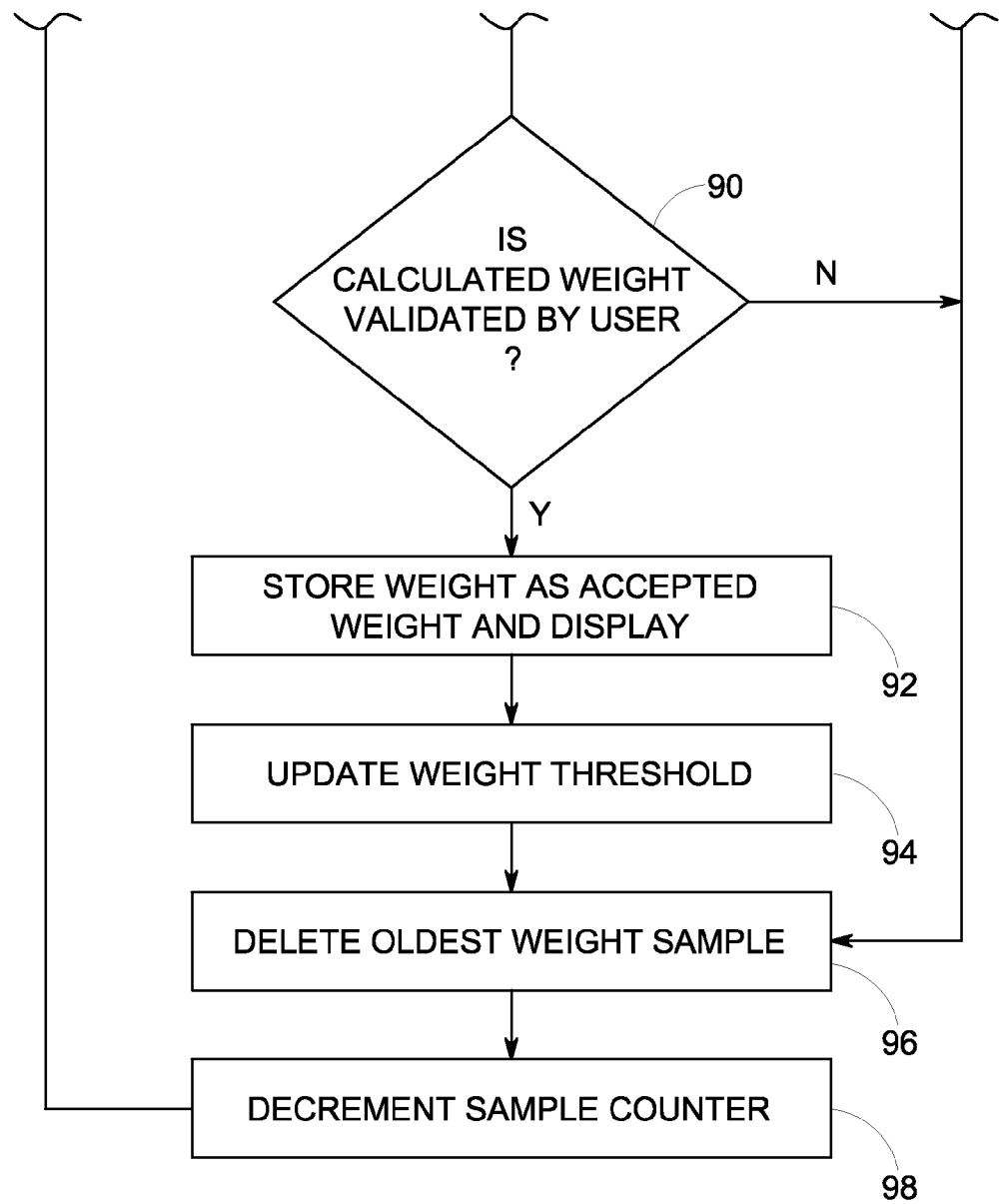
FIG. 4 is a flowchart illustrating the operating sequence carried out by the control unit of the weighing system.

FIG. 4 illustrates the operating sequence carried out by the control unit 36 of the weighing system 32. Although the operational sequence set forth in FIG. 4 provides one exemplary embodiment of the disclosure, it should be understood that the operational sequence could be varied while operating within the scope of the present disclosure.

Initially, the control unit acquires a weight measurement from the sensor 44 shown in FIG. 3 and stores the retrieved restored weight sample in a memory unit 54 along with a time stamp, as illustrated in step 56. In the embodiment illustrated in FIG. 3, the sensor 44 acquires a weight measurement on a periodic basis, such as at a sampling rate of one sample per second. Although one possible sample rate is described, it should be understood that the sensor 44 could be configured to acquire samples at a slower or faster rate while operating within the scope of the present disclosure.

Once the control unit 36 receives a weight sample from the sensor 44, the control unit proceeds to step 58 and increments a sample counter. During the initial processing sequence, the control unit acquires a predetermined number of historic weight samples before the system begins the process of calculating the weight of an infant. In the initial examples to be set forth below, the system acquires a predetermined number of samples, represented by variable N. In step 60, the system determines whether the predetermined number of samples N has been acquired. If the predetermined number of historic weight samples N have not yet been acquired, the system returns to step 56 and acquires additional weight measurements from the sensor and stores the measurements in the memory unit.

Figure 5:
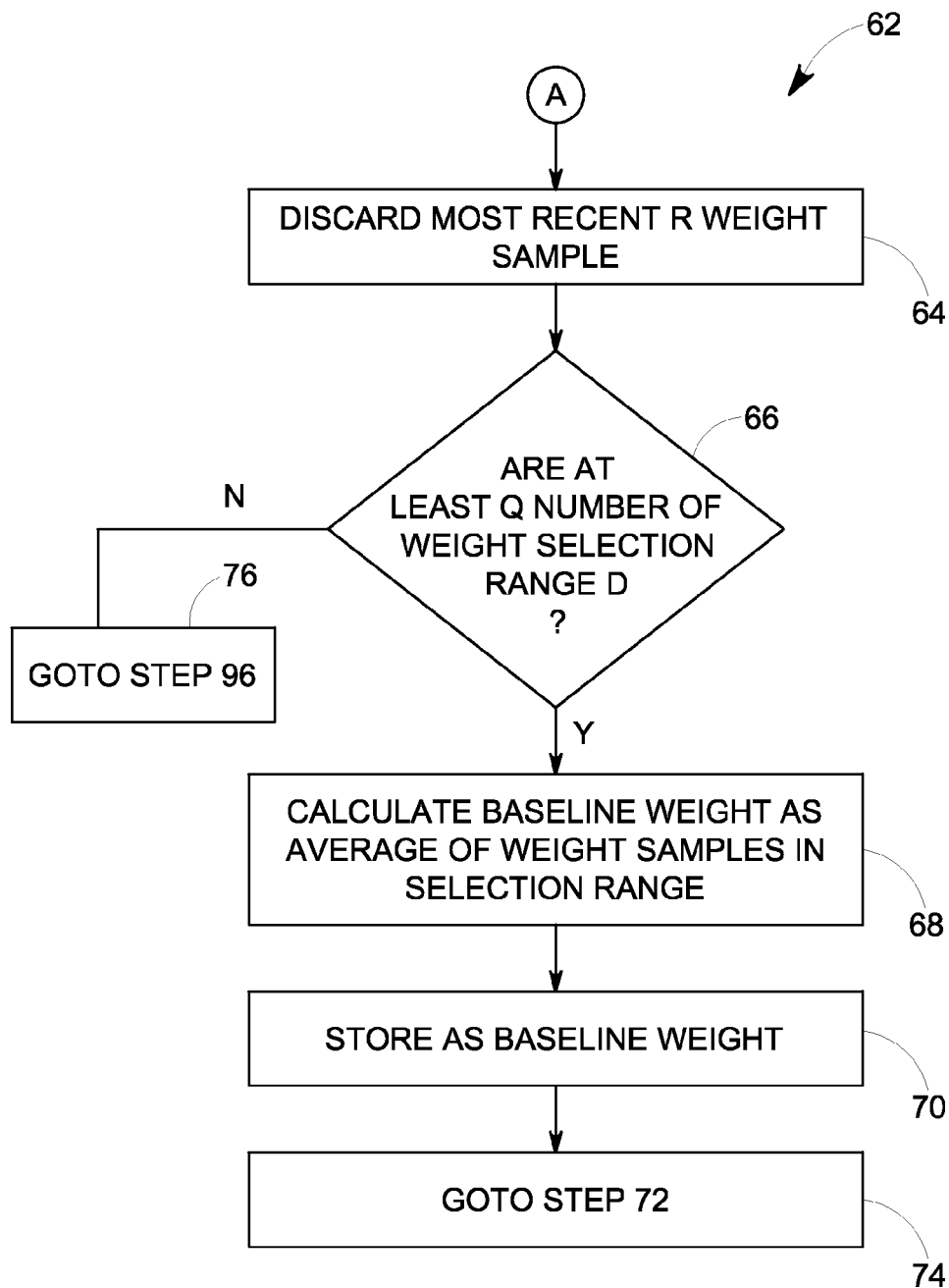
FIG. 5 is a flowchart illustrating the portion of the weighing algorithm used to determine the baseline weight.

When the system determines in step 60 that the required number of historic weight samples N have been acquired, the system proceeds to step 62, during which the system calculates a baseline weight. The baseline weight calculated in step 62 will include the weight of the support platform 40, the mattress 42 and any item that is positioned on the mattress, which in some cases will include the infant and any sensors or peripheral devices associated with the infant during monitoring and care of the infant within the infant care device 10. The process required to calculate the baseline weight in step 62 is further illustrated in the flowchart of FIG. 5.

Examples 1 and 2 set forth below illustrate two different sample sets of weight measurements obtained from the sensor and stored in the memory unit following step 60. Although these sample sets are included for illustrative purposes, it should be understood that the values represented by the sets of readings are for illustrative purposes only and do not necessarily correspond to actual weight values from the sensor 44.

EXAMPLE 1

"Base Line" Weight Established

| 50 Samples: | | | | | | | | | |
|---|---|---|---|---|---|---|---|---|---|
| 2150 | 2151 | 2179 | 2180 | 2152 | 2151 | 2152 | 2150 | 2151 | 2150 |
| 2152 | 2153 | 2150 | 2150 | 2150 | 2151 | 2154 | 2150 | 2151 | 2185 |
| 2151 | 2152 | 2152 | 2150 | 2151 | 2152 | 2152 | 2152 | 2152 | 2150 |
| 2153 | 2152 | 2142 | 2150 | 2152 | 2152 | 2152 | 2151 | 2150 | 2151 |
| 2151 | 2151 | 2122 | 2150 | 2150 | 1551 | 1554 | 1551 | 1552 | 1551 |

N is 50
R is 5
Q is 35
D is 10 grams
RQ is 5
RD is 5 grams

EXAMPLE 2

"Base Line" Weight not Established

| 50 Samples: | | | | | | | | | |
|---|---|---|---|---|---|---|---|---|---|
| 2150 | 2151 | 2179 | 2180 | 2152 | 2111 | 2152 | 2150 | 2151 | 2141 |
| 2110 | 2153 | 2150 | 2150 | 2150 | 2111 | 2154 | 2150 | 2151 | 2185 |
| 2151 | 2113 | 2114 | 2150 | 2151 | 2152 | 2152 | 2152 | 2152 | 2150 |
| 2153 | 2152 | 2142 | 2150 | 2152 | 2180 | 2152 | 2151 | 2150 | 2151 |
| 2180 | 2151 | 2122 | 2150 | 2180 | 1548 | 1554 | 1535 | 1552 | 1561 |

N is 50
R is 5
Q is 35
D is 10 grams.
RQ is 5
RD is 5 grams

In the illustrative set of historic weight samples of Examples 1 and 2 above, the number of samples N stored in the memory unit is 50.

Once the sample set shown in Example 1 has been stored, the control unit 36 proceeds to step 64 in which the control unit disregards the most recent R number of weight samples. In Example 1 shown above, R is 5 and represents the five most recent weight samples obtained from the sensor. The most recent weight samples R are not considered during the calculation of the baseline weight since these samples will be used in the calculation of the recent weight, as will be described in greater detail below with reference to FIG. 6.

Referring back to FIG. 5, once the most recent R weight samples have been discarded, the system proceeds to step 66 and determines whether at least a predetermined number of weight samples Q are within a selection range of each other. The selection range is referred to by variable D. The selection range is utilized by the system to make sure that at least a predetermined number Q of the historic weight samples N are within a certain range of each other such that the baseline weight calculation is valid. As shown in Example 1, the required number of weight samples Q is 35 and the selection range D is 10 grams.

In the embodiments illustrated above, the most recent number of samples R discarded in the baseline weight calculation are shown in bold. Once the most recent number of samples (five) are discarded, forty-five of the fifty samples N remain. In Example 1 illustrated above, five of the weight samples, which are underlined, fall outside of the ten gram range D. However, forty samples remain, which is greater than the required number Q. The forty samples within the selection range D are then added and averaged to create a baseline weight, as illustrated in step 68. In the embodiment shown in Example 1, the baseline weight is calculated as 2151.175 and is stored in step 70 as the baseline weight. Once the baseline weight has been stored in step 70, the system proceeds to step 72, as illustrated in step 74 of FIG. 5.

In the sample set shown in Example 2, the sample size N is again 50, the number of the most recent weight samples R discarded for the baseline weight calculation is five, the number of samples Q required to be within the selection range D is 35 and the selection range is again ten grams.

In the sample set shown in Example 2, only thirty-one samples are within the selection range D. Since the number of samples within the selection range is less than the required number Q (35), the system determines in step 66 that the required number of samples are not within the selection range and proceeds to step 76. Since the required number of samples were not present, the system does not calculate a baseline weight and proceeds to step 96 in FIG. 4.

Figure 6:
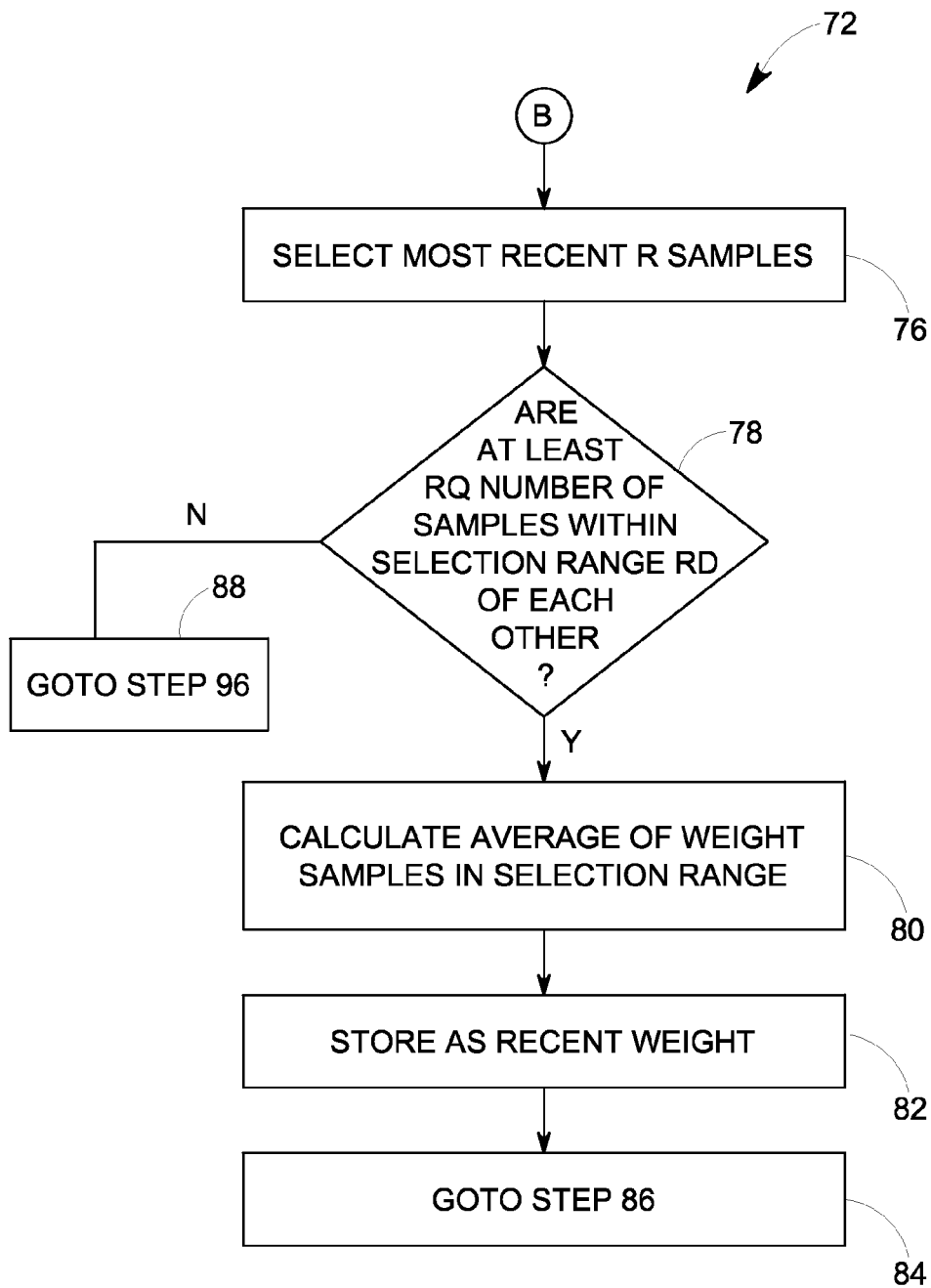
FIG. 6 is a flowchart illustrating a portion of the weighing algorithm used to calculate a recent weight estimate.

Referring back to FIG. 4, if the system calculates a baseline weight and stores the weight in the memory unit, the system proceeds to step 72 to calculate a recent weight estimate. The steps required to calculate the recent weight estimates are illustrated in the flowchart of FIG. 6.

Initially, the processing unit selects the most recent R samples for use in determining a recent weight estimate. In the sample set of Example 1, the number of most recent samples R is five and these samples are shown in bold.

Once the most recent samples R have been selected, the system determines in step 78 whether at least a select number RQ of the samples are within a selection range RD of each other. In the sample set of Example 1, RQ is set to five and the selection range RD is set to 5 grams. As can be understood in the sample set shown in Example 1, all five of the most recent samples R fall within the selection range RD. The span between the highest sample (1551) and the highest sample (1554) is only 3 grams.

Step 78 insures that the system does not proceed to step 80 until at least RQ number of the most recent samples are within a selection range of each other. Thus, the system will not calculate a recent weight estimate until at least a certain number of the most recent samples are within a selected range of each other. This prevents brief changes in the weight from causing the system to proceed to the weight determination cycle.

Once the system proceeds to step 80, the system calculates the average weight of the RQ number of samples that are within the selection range RD of each other. Once the average weight has been calculated in step 80, the system saves this value as a recent weight estimate, as illustrated in step 82. Once the recent weight has been stored, the system proceeds to step 84, which returns the system to processing step 86 in FIG. 4.

Referring back to FIG. 6, if the system determines in step 78 that the required number of samples RQ is not within the selection range, the system proceeds to step 88 and returns to step 96 in FIG. 4. As an illustrative example, in the sample set of Example 2, only three of the most recent R five samples is within the selection range RD of 5 grams. Since at least RQ number of samples are not within the selection range RD, the system proceed to step 88 and does not calculate a new recent weight value.

Referring back to FIG. 4, once the baseline weight and the recent weight estimate have been calculated in steps 62 and 72, respectfully, the system proceeds to step 86 to determine whether the recent weight estimate is a valid weight estimate. In step 86, the system determines whether the recent weight estimate is greater than or less than the baseline weight by more than a weight threshold. If the difference exceeds the weight threshold, the system determines that the recent weight estimate is a possible valid estimate for the weight of the infant. If the difference does not exceed the weight threshold, the estimate may just be a variation in the baseline due to possible other factors other than either placement of the infant on the mattress or removal of the infant from the mattress.

In step 86, the system compares the recent weight estimate to the baseline weight and determines whether the difference is greater than a weight threshold amount T. As an illustrative example, if the baseline weight estimated in step 62 is 2200 grams and the recent weight estimate in step 72 is 4500 grams, the difference between the two estimates is 2300 grams. In the first iteration of the process shown by the flowchart in FIG. 4, the weight threshold may be set at a low value, such as 300 grams. In the embodiment described, the difference between the recent weight estimate and the baseline weight is greater than the weight threshold and the system will proceed to step 88.

In step 88, the processing unit generates a calculated infant weight measurement as the difference between the baseline weight and the recent weight estimate. As can be understood by the above description, if the baseline weight calculated in step 62 includes the infant on the mattress, once the infant is removed, the system will then calculate a recent weight estimate in step 72 which is less than the baseline weight. If the difference between these two values is greater than the weight threshold, the system will proceed to step 88 to calculate an infant weight measurement. Conversely, if the infant is not on the mattress, the calculated baseline weight in step 62 will be less than the recent weight estimate which is generated when the infant is placed on the mattress. In such an example, the recent weight estimate will exceed the baseline weight by more than the weight threshold and the system will again calculate the weight of the infant in step 88.

Once the system calculates the weight of the infant, the weight is displayed for validation by the user, as illustrated in step 88. It is contemplated that the weight could be shown on various different displays either located remotely from the infant care device or on the display 28 associated with the infant care device. In step 90, the user is questioned as to whether the calculated infant weight measurement from step 88 is a valid weight.

If the user determines that the calculated weight is valid, the system stores the calculated weight in the memory and displays the weight of the patient as an accepted weight in step 92. If the calculated weight is not validated by the user in step 90, the system proceeds to step 96, as will be described below.

Once the weight has been validated and stored, the system updates the weight threshold T in step 94. As previously described with reference to step 86, the weight threshold is used by the system to determine whether the recent weight estimate is an actual weight or a slight variation from the baseline. In accordance with the present disclosure, the weight threshold is determined as a percentage of the accepted weight stored in step 92. In the embodiment previously described, the accepted weight was 2300 grams. In an illustrative example, the percentage of weight P1 used to set an updated weight threshold is 80% such that the weight threshold will be updated to be 80% of the accepted weight, which results in an adjusted threshold of 1840 grams.

Once the weight threshold has been updated in step 94, the system deletes the oldest weight sample in step 96 and decrements the sample counter in step 98. The oldest weight sample is discarded and the sample counter decreased such that the system returns to step 56 to begin the process of monitoring for a change between the baseline weight and the recent weight estimate, which indicates the removal or placement of an infant on the mattress.

In another illustrative example, if the weight estimate is 1900 grams and the baseline is 1500 grams with a weight threshold set at 600 grams, the system will determine in step 86 that the recent weight estimate is not greater than or less than the baseline by the weight threshold in step 86. In such an example, the system proceeds to step 96 and obtains additional samples from the weight sensor. If the recent weight estimate remains the same, the recent weight estimate will eventually become the new baseline after the desired number of samples are obtained.

As described above, values are shown for the recent weight estimate, the baseline estimate and samples taken from the weight sensor. The values used are for illustrative purposes only and are not meant to limit the scope of the present disclosure.

As can be understood by the above flowcharts, the system will generate a calculated weight and display the weight to the user for validation upon either placement of an infant on a mattress or upon removal of the infant from the mattress. Either event will result in the recent weight estimate varying from the baseline weight by more than the weight threshold. Thus, every time the infant is placed on the mattress or removed from the mattress, the system will present the user with a calculated infant weight measurement. The user can then either validate this measurement or discard the measurement as desired. It is contemplated that the automated process described in FIG. 4 could be turned off from the infant care device if the infant is being placed on and removed from the mattress on regular intervals. However, the system and method described allows the weight of the infant to be calculated each time the infant is either placed on the mattress or removed therefrom.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims

I claim:

1. A method of determining the weight of an infant, the method comprising the steps of:
   obtaining a predetermined number of historic weight samples from a sensor positioned to detect the weight of a support platform and objects positioned on the support platform;
   setting a baseline weight in a control unit, wherein the baseline weight is an average of the historic weight samples;
   obtaining a predetermined number of current weight samples from the sensor, wherein the current weight samples are more recent than the historic weight samples;
   generating a recent weight estimate in the control unit, wherein the recent weight estimate is an average of the current weight samples; and
   generating a calculated infant weight measurement as the difference between the baseline weight and the recent weight estimate only when the difference exceeds a weight threshold.

2. The method of claim 1 wherein the historic weight samples are a predetermined number of most recent weight samples prior to the current weight samples.

3. The method of claim 1 wherein the weight measurement is generated based on a positive or a negative difference between the baseline weight and the recent weight.

4. The method of claim 1 further comprising the steps of:
   presenting the calculated infant weight measurement to a user and requesting validation of the calculated infant weight measurement; and
   storing the calculated infant weight measurement in the control unit as an accepted weight when validated by the user.

5. The method of claim 4 further comprising the steps of:
   calculating an updated weight threshold as a percentage of the accepted weight; and
   storing the updated weight threshold in the control unit for use in subsequent weight calculations.

6. The method of claim 4 further comprising the steps of:
   comparing the accepted weight with a historic weight stored in the control unit; and
   generating a notification to the user when the difference between the accepted weight and the historic weight is greater than an alarm percentage of the historic weight.

7. The method of claim 4 wherein the weight measurement is manually validated by the user.

8. The method of claim 1 wherein the baseline weight is calculated based on only the historic weight samples within a selected range from each other.

9. The method of claim 8 wherein the current weight samples are not used to calculate the baseline weight.

10. A method of determining the weight of an infant comprising the steps of:
    obtaining a predetermined number of historic weight samples in a control unit from a sensor positioned to detect the weight of a support platform and objects positioned on the platform;
    setting a baseline weight in the control unit, wherein the baseline weight is an average of the historic weight samples;
    automatically generating a calculated infant weight measurement upon placement of the infant on the support platform or removal of the infant from the support platform; and wherein the step of automatically calculating the infant weight measurement comprises:
    obtaining a predetermined number of current weight samples from the sensor, wherein the current weight samples are more recent than the historic weight samples;
    generating a recent weight in the control unit, wherein the recent weight is an average of the current weight samples; and
    calculating a difference between the baseline weight and the recent weight,
    wherein the calculated infant weight is automatically generated when the difference exceeds a weight threshold.

11. The method of claim 10 wherein the historic weight samples are the predetermined number of most recent weight samples prior to the current weight samples.

12. The method of claim 10 wherein the weight measurement is generated based on a positive or a negative difference between the baseline weight and the recent weight.

13. The method of claim 12 further comprising the steps of:
    calculating an updated weight threshold as a percentage of the accepted weight; and
    storing the updated weight threshold in the control unit for use in subsequent weight calculations.

14. The method of claim 12 further comprising the steps of:
    comparing the accepted weight with a historic weight stored in the control unit; and
    generating a notification to the user when the difference between the accepted weight and the historic weight is greater than an alarm percentage of the historic weight.

15. A system for determining the weight of an infant, comprising:
    a support platform sized to receive and support the infant;
    a sensor positioned to detect the weight of the support platform and objects positioned on the support platform; and
    a control unit in communication with the sensor to receive a weight signal from the sensor, wherein the control unit is programmed to:
      obtain a predetermined number of historic weight samples from the sensor;
      set a baseline weight in the control unit, wherein the baseline weight is an average of the historic weight samples;
      obtain a predetermined number of current weight samples from the sensor, wherein the current weight samples are more recent than the historic weight samples;
      generate a recent weight estimate in the control unit, wherein the recent weight estimate is an average of the current weight samples; and
      generate a calculated infant weight measurement as the difference between the baseline weight and the recent weight estimate when the difference exceeds a weight threshold.

16. The system of claim 15 further comprising an input device coupled to the control unit, wherein the calculated infant weight measurement is presented to a user and the user validates the calculated infant weight measurement through the input device.

17. The system of claim 16 wherein the control unit stores the calculated infant weight measurement in the control unit as an accepted weight when validated by the user.

18. The system of claim 17 wherein:
    the control unit is further programmed to calculate an updated weight threshold as a percentage of the accepted weight; and
    store the updated weight threshold in the control unit for use in subsequent weight calculations.

19. The system of claim 15 further comprising a display coupled to the control unit for displaying the calculated infant weight measurement.

* * * * *